(12) United States Patent
Karimi et al.

(10) Patent No.: US 6,252,138 B1
(45) Date of Patent: Jun. 26, 2001

(54) PATHOGEN-INDUCED PLANT PROMOTERS

(75) Inventors: Mansour Karimi; Nathalie Barthels, both of Ghent; Godelieve Gheysen, Merelbeke, all of (BE)

(73) Assignee: Plant Genetic Systems, N.V. (BE)

( * ) Notice: Subject to any disclaimer, the term of this patent is extended or adjusted under 35 U.S.C. 154(b) by 0 days.

(21) Appl. No.: 09/341,678

(22) PCT Filed: Jan. 19, 1998

(86) PCT No.: PCT/EP98/00388

§ 371 Date: Jul. 20, 1999

§ 102(e) Date: Jul. 20, 1999

(87) PCT Pub. No.: WO98/31822

PCT Pub. Date: Jul. 23, 1998

(30) Foreign Application Priority Data

Jan. 20, 1997 (EP) .................................. 97200103

(51) Int. Cl.[7] ........................ C12N 15/09; C12N 15/31; C12N 15/82; C12N 15/15; A01H 5/00
(52) U.S. Cl. ......................... 800/279; 800/278; 800/287; 800/285; 800/288; 800/306; 800/317.2; 536/23.1; 536/24.1; 536/23.7; 536/23.6; 435/69.1; 435/418; 435/419; 435/320.1; 435/468; 435/480; 435/199
(58) Field of Search ................................... 800/279, 278, 800/287, 306, 317.2, 285, 288; 536/23.1, 24.1, 23.7, 23.6; 435/69.1, 418, 419, 320.1, 468, 480, 199

(56) References Cited

U.S. PATENT DOCUMENTS 5,494,813 * 2/1996 Hepher et al. ..................... 435/172.3
5,770,786 * 2/1996 Sijmons ............................ 800/200

FOREIGN PATENT DOCUMENTS

WO 92/21757 * 12/1992 (WO).
93/06710    4/1993  (WO).
WO 93/10251 * 5/1993  (WO).
94/10320    5/1994  (WO).

OTHER PUBLICATIONS

Kim et al. Plant Molecular Biology, vol. 24, pp. 105–117, 1994.*
Gheysen, G., et al., "The exploitation of nematode–responsive plant genes in novel nematode control methods", *Pesticide Science*, 47 (1), 1996, 95–101, XP000629097.
Goddijn, O.J.M., et al., "Differential gene expression in nematode–induced feeding structures of transgenic plants harbouring promotor–gusA fusion constructs", *Plant Journal*, vol. 4, No. 5, Jan. 1, 1993, pp. 863–873, XP002000605.
Barthels, N., et al., "Isolation and analysis of nematode–induced genes in Arabidopsis thaliana through in vivo.beta.–glucuronidase fusions", *Med.Fac. Landbouwkd*, Toegepaste Biol. Wete. (Univ. Gent), 1994, pp. 757–62, XP002000607.

* cited by examiner

*Primary Examiner*—David T. Fox
*Assistant Examiner*—Medina A. Ibrahim
(74) *Attorney, Agent, or Firm*—Hunton and Williams

(57) ABSTRACT

New pathogen-induced promoters are provided, particularly nematode-induced promoters, which are characterized by their selective induction of expression in the vicinity of the pathogen infection sites, such as the fixed feeding cells induced by infection of the plant by nematodes. Further provided are chimeric genes comprising these promoters as regulatory elements, as well as transgenic plants, comprising those chimeric genes, which are less susceptible to pathogen infections.

26 Claims, No Drawings

SEQUENCE LISTING

<160> NUMBER OF SEQ ID NOS: 9

<210> SEQ ID NO: 1
<211> LENGTH: 24
<212> TYPE: DNA
<213> ORGANISM: Arabidopsis thaliana

<400> SEQUENCE: 1
ccagcgtgga ccgcttgctg caac                                          24

<210> SEQ ID NO: 2
<211> LENGTH: 25
<212> TYPE: DNA
<213> ORGANISM: Arabidopsis thaliana

<400> SEQUENCE: 2
gtattgccaa cgaaccggat acccg                                         25

<210> SEQ ID NO: 3
<211> LENGTH: 22
<212> TYPE: DNA
<213> ORGANISM: Arabidopsis thaliana

<400> SEQUENCE: 3
cccagtcacg acgttgtaaa ac                                            22

<210> SEQ ID NO: 4
<211> LENGTH: 630
<212> TYPE: DNA
<213> ORGANISM: Arabidopsis thaliana
<220> FEATURE:
<221> NAME/KEY: Primer 2
<222> LOCATION: 1..24
<223> OTHER INFORMATION: region corresponding to oligonucleotide
      primer 2
<220> FEATURE:
<221> NAME/KEY: Primer 1
<222> LOCATION: 606..630
<223> OTHER INFORMATION: region corresponding to oligonucleotide
      primer 1
<220> FEATURE:
<221> NAME/KEY: SspI
<222> LOCATION: 43..48
<223> OTHER INFORMATION: recognition site SspI
<220> FEATURE:
<221> NAME/KEY: PvuII
<222> LOCATION: 571..576
<223> OTHER INFORMATION: recognition site for PvuII
<220> FEATURE:
<221> NAME/KEY: StyI
<222> LOCATION: 296..301
<223> OTHER INFORMATION: recognition site for StyI
<220> FEATURE:
<221> NAME/KEY:
<222> LOCATION: 466..630
<223> OTHER INFORMATION: homology to the left side of the T-DNA of
      pdeltaGusBin19
<220> FEATURE:
<221> NAME/KEY:
<222> LOCATION: 436..465
<223> OTHER INFORMATION: filler DNA generated during T-DNA insertion

<400> SEQUENCE: 4
gtattgccaa cgaaccggat acccgtccgc aaggtgcacg ggaatattaa ctaaattgtc    60
ccaattcatc aaacaaactt cactattttt ctaaagatgg atgaaaatta atcagaggtc   120
ttttgagatt tgatggttca attcagtcgt gaaattacat tatttaaaga aaactagatt   180

| caaaacaaaa taaataggtg ttagaaaagg tagattcgtt tcaccgaacg ataaagaaaa | 240 |
| aaaaattatt attccaccaa aaaaaaagaa aaaaatatat taaattttg actaccctag | 300 |
| ggttgcttct tggatacgtc taggatctca atagcatagt ggattttttt ttaaaaggag | 360 |
| aaacaaaatt attttatttt ttaaaaaagc gagaaatcag gataatcaat ggttagaata | 420 |
| ataataattt cactcggaac cctgtgactc gtgaccacaa tttgtttata ttgtggtgta | 480 |
| aacaaattga cgcttagaca acttaataac acattgcgga cgttttaat gtactggggt | 540 |
| ggttttctt ttcaccagtg agacgggcaa cagctgattg cccttcaccg cctggccctg | 600 |
| agagagttgc agcaagcggt gccacgctgg | 630 |

```
<210> SEQ ID NO: 5
<211> LENGTH: 4160
<212> TYPE: DNA
<213> ORGANISM: Arabidopsis thaliana
<220> FEATURE:
<221> NAME/KEY: MAKAR17
<222> LOCATION: 945..968
<223> OTHER INFORMATION: region corresponding to oligonucleotide
      MAKAR17
<220> FEATURE:
<221> NAME/KEY:
<222> LOCATION: 1444..1445
<223> OTHER INFORMATION: insertion point of T-DNA
      insertion in the line ARM1
<220> FEATURE:
<221> NAME/KEY:
<222> LOCATION: 1418..1570
<223> OTHER INFORMATION: putative open reading frame
```

<400> SEQUENCE: 5

| gtaactttcc taattaacgt taagattagt gttttttata cattcgtagc accaattatt | 60 |
| gatgtaggcg gatatactat ataatttgat aaataagatt atagtactac tccatatgtt | 120 |
| taaggttag tggacccaaa gaaatcgga atagatcaaa gtgaagggcc cggattagta | 180 |
| taactcctgc atgcctcatg gatcttttt ataaacagcg gcgatcccga tgactaaaga | 240 |
| agaaaagcta aaggttaaac aaagtcaaga tttgaatttc tctttttgtt cttttttac | 300 |
| cgatttcct atatataatt tgctttatcc ttttgaatt tgtttacctc ggctttgcga | 360 |
| aaactaaatt tgtttttgat tttgcgaaac aaaaaataag gaaagaagaa gcatgcacgt | 420 |
| gtggtgtaca agagtgagtg gtgacccact ctcgtataat ttgcttgcaa acttagctct | 480 |
| ccttttgcat gcttccatga ttttgtttcc ccctttttt tagtaaccta ttttaattta | 540 |
| attttcttcg accgtatttc ataataatgt ttcaagttta cagatattac tagttactac | 600 |
| gacctgacta ttataggatc agtcctagtc aaaacatttt ggttgttttt ttcgcctagt | 660 |
| ttatttctta attttggaat tggataataa agaaaagcgt ctcaatcaaa ggtcggccaa | 720 |
| aagacgcgcg gctcggtgtt ggcgttggtt tgcggacgga catcaatggt ggcgtatgtt | 780 |
| tctctctacg gacgtctttg tgcaaatata ttctacacgt gtcctctttt tgtcggctta | 840 |
| tgggtcccat taactaaact gtccacgtgg cactatctca aattcaatgg cccacgcttc | 900 |
| atccttcgtt actccctcct tcccttgctg ccgttagatc gcgcgagcaa ggaagaggca | 960 |
| aagtacatta tgcttgtttt tccttttca atgttattag taattaatat aaaaaaaaat | 1020 |
| tattaattaa taatttttctg tataccaccg atatattaac taaattgtcc caattcatca | 1080 |
| aacaaacttc actattttc taaagatgga tgaaaattaa tcagaggtct tttgagattt | 1140 |
| gatggttcaa ttcagtcgtg aaattacatt atttaaagaa aactagattc aaaacaaaat | 1200 |
| aaataggtgt tagaaaaggt agattcgtat caccgaacga taaagaaaaa aaaattatta | 1260 |

```
ttccaccaaa aaaaaagaaa aaaatatatt aaatttttga ctaccctagg gttgcttctt    1320
ggatacgtct aggatctcaa tagcatagtg gatttttttt taaaaggaga aacaaaatta    1380
ttttattttt taaaaaagcg agaaatcagg ataatcaatg gttagaataa taataatttc    1440
actccggtca cgagtcacag ggttccgagt caccagtctt ccactatatc acgtaatccc    1500
gcggcggtac gccaaaacat ttcagtattt tagagtgttg ggatatacaa taacatatca    1560
tatacagtaa gtcaaatctt cgaattttga attataaaag cccatcaacc aacactttt    1620 atatgaaaaa acaatagaac aaatagaggc gatgtataat actctagtca tacctaagtc    1680
ttactcatat tcatagaaca tcagaatgta ttaggcgaag tgactataga tatatagttt    1740
gaattgcatg tggattcgtt taattggttg agttaggtga ctaatttgga ccatttaaaa    1800
agatagagag tgttccctaa caagagaaaa ccttctagag gagttgacaa ggcatgaatc    1860
aagggataat attcacgttg cttctttctt ggatacttat gtctcgtgat taattcacaa    1920
gtagcaatca attccctaat taaatgcctt tttgttaatt taattggaaa aaaaaatcac    1980
tcaaacgcca ctcgtatcgc atgtgttgac ccacttaaga tttctttcgc aattctaaaa    2040
tgttgtgtgg aagagttaaa aacaaaatcg ttaaataata accgttgcgt tggtatttgc    2100
acatgggtaa gtcaaagtaa acgcattttg ggatcttatt ttatttatta atcgccgcat    2160
caaacataat accgattaat ataaatccct ccgatggtag ctagtcatta acttatagtc    2220
attaatatca tttactaata tctctacata taaattttg tcttctacat atcggacaac    2280
gatccagttt agtttgatat ttttcttat atgtaaaaag gttcaacgaa tttgaaatgt    2340
gtggtagcac ttatcctcct cctaaatcga ttcctacctc tctaatacgg ttaaaaaaaa    2400 aaaaaaaga caatagctaa ccgaaatttt ggatcatatt gtacatagaa gtgaaacgaa    2460
gtcgcaaggc aaatattaat agatattttc ggattttaaat gtcggtataa tcaaaattta    2520
taggaattac atacgaaagt aatgaaggat caccgaaaac attttctaaa ataaaataac    2580
cgcaatgtaa accatgagtt agtgtacaga taacatgtta tagctaaact atatgataaa    2640
aaaaactata tgcttaattt tattaagcaa gtaaacaaaa tatcacataa ttatgttttg    2700
gaagaatcgg aaaccatata tgtttgagta atcaaatgag cccgtttata agcccattta    2760 aagacttttac ttgccatctc tacacggtgt taaagaataa atgtgtagtg ccatgttaat    2820
attgttgaac cccaaatcaa cgtcgagata ataaaatgtc ggaccatttc atcacaacca    2880
attcgtgtca tctcaaataa attaaagggc taaatgatac gtggccatca acatttgta    2940 tctgttatct atcattatca cagagtgaca ctgtagtcca acagcaggat ttaaaagcac    3000
atagtgacat aacacagttt taccaattat ttgaaagaat tacaatgaaa agtaaattac    3060
atcgttataa tacgtactat gaagctagta gtcttctcga taaattttct gcatatccac    3120
tattgatgcc tagaactatt cgaaaataat cggtatattc tttattttgg tcatcgcaaa    3180
ttttaattta tttgtaacac cctaaatgga gagcgtagta acaacacgtc aacaacaaat    3240
aatatggaaa gcacgaatga aaaaacaaaa tatagctaac tcactgtgtt aaatagttta    3300
aggattaatt ttgatatttc aagactaaaa ttcagttct ttcactgtaa tttccaaatc    3360
atagtttgca attatgaatt ttcaaatgaa tagaaatatt gaaactttca caagttcgaa    3420
ggtgagcctg aacttcgaat ttggatgctt ccattatatg gactaaaaat tcggtatttg    3480
aattcgtggc ccacgcactt tcacagccca acgttaaaca tcttttcaa cagtgttttg    3540 tccctttatt ggtaaaaaat acctgttacc tccctacatt tgtattttct ccaaccgact    3600
```

-continued

| | |
|---|---|
| gaacttaatt ttattgatat catgtttaca acatagttcc tttacaacct ttttaagaaa | 3660 |
| tgacccttg ttctttgcta atgtagcaca caaaaactat tcccatggaa caattatcat | 3720 |
| gttttttttt tgccgaacca actgtcatct gttatttaga taagcatata atacatatat | 3780 |
| attttttgata tttaattttc tgcgaagtct acactctaca gcagcaagat aaaccaaatt | 3840 |
| cctttctat ataagcaaca caagacaatc acacgagata ataaaaaaa aacacgaaca | 3900 |
| aataaaaact aaaaacacgt aaaatgcaac aagatataca aaaatatat gaaggttttt | 3960 |
| aaacacagtc agtttcggtc aaaacctgaa ccattgtctg cataactctc actttcattt | 4020 |
| ccaaagccaa gatataatct gccgtttgtc taaagagtcc atctaaacct tctgatgttt | 4080 |
| tggtgttggg aacaagctct tttagcgtct tcactcgtct gtgtattgcg cgacaagtct | 4140 |
| tctagagcgg ccgccaccgc | 4160 |

<210> SEQ ID NO: 6
<211> LENGTH: 25
<212> TYPE: DNA
<213> ORGANISM: Arabidopsis thaliana

<400> SEQUENCE: 6
gactgaatgc ccacaggccg tcgag                                      25

<210> SEQ ID NO: 7
<211> LENGTH: 24
<212> TYPE: DNA
<213> ORGANISM: Arabidopsis thaliana

<400> SEQUENCE: 7
gagcaaggaa gaggcaaagt acat                                       24

<210> SEQ ID NO: 8
<211> LENGTH: 1273
<212> TYPE: DNA
<213> ORGANISM: Arabidopsis thaliana
<220> FEATURE:
<221> NAME/KEY: MAKAR17
<222> LOCATION: 1..24
<223> OTHER INFORMATION: region corresponding to oligonucleotide
      MAKAR17
<220> FEATURE:
<221> NAME/KEY: SspI
<222> LOCATION: 109..115
<223> OTHER INFORMATION: recognition site for SspI
<220> FEATURE:
<221> NAME/KEY: StyI
<222> LOCATION: 361..366
<223> OTHER INFORMATION: recognition site for StyI
<220> FEATURE:
<221> NAME/KEY:
<222> LOCATION: 501..531
<223> OTHER INFORMATION: filler DNA generated upon T-DNA insertion
<220> FEATURE:
<221> NAME/KEY:
<222> LOCATION: 532..1273
<223> OTHER INFORMATION: region corresponding to the left region of
      the T-DNA of pDeltaGusB...
<220> FEATURE:
<221> NAME/KEY: SmaI
<222> LOCATION: 1118..1193
<223> OTHER INFORMATION: recognition site for SmaI
<220> FEATURE:
<221> NAME/KEY: MAKAR4
<222> LOCATION: 1249..1273
<223> OTHER INFORMATION: region corresponding to oligonucleotide
      MAKAR4

<400> SEQUENCE: 8

```
gagcaaggaa gaggcaaagt acattatgct tgtttttcct ttttcaatgt tattagtaat        60
taatataaaa aaaaattatt aattaataat tttctgtata ccaccgatat attaactaaa       120
ttgtcccaat tcatcaaaca aacttcacta tttttctaaa gatggatgaa aattaatcag       180
aggtcttttg agatttgatg gttcaattca gtcgtgaaat tacattattt aaagaaaact       240
agattcaaaa caaaataaat aggtgttaga aaaggtagat tcgtatcacc gaacgataaa       300
gaaaaaaaaa ttattattcc accaaaaaaa aagaaaaaaa tatattaaat ttttgactac       360
cctagggttg cttcttggat acgtctagga tctcaatagc atagtggatt tttttttaaa       420
aggagaaaca aaattatttt attttttaaa aaagcgagaa atcaggataa tcaatggtta       480
gaataataat aatttcactc ggaaccctgt gactcgtgac cacaatttgt ttatattgtg       540
gtgtaaacaa attgacgctt agacaactta ataacacatt gcggacgttt ttaatgtact       600
ggggtggttt ttcttttcac cagtgagacg ggcaacagct gattgcccct caccgcctgg       660
ccctgagaga gttgcagcaa gcggtccacg ctggtttgcc ccagcaggcg aaaatcctgt       720
ttgatggtgg ttccgaaatc ggcaaaatcc cttataaatc aaaagaatag cccgagatag       780
ggttgagtgt tgttccagtt tggaacaaga gtccactatt aaagaacgtg gactccaacg       840
tcaaagggcg aaaaaccgtc tatcagggcg atggcccact acgtgaacca tcacccaaat       900
caagtttttt ggggtcgagg tgccgtaaag cactaaatcg gaaccctaaa gggagccccc       960
gatttagagc ttgacgggga aagccggcga acgtggcgag aaaggaaggg aagaaagcga      1020
aaggagcggg cgccattcag gctgcgcaac tgttgggaag ggcgatcggt gcgggcctct      1080
tcgctattac gccagctggc gaaggggga tgtgctgcaa ggcgattaag ttgggtaacg       1140
ccagggtttt cccagtcacg acgttgtaaa acgacggcca gtgaattccc gggtggtcag      1200
tcccttatgt tacgtcctgt agaaaccca acccgtgaaa tcaaaaaact cgacggcctg       1260
tgggcattca gtc                                                         1273
```

<210> SEQ ID NO: 9
<211> LENGTH: 100
<212> TYPE: DNA
<213> ORGANISM: Arabidopsis thaliana
<220> FEATURE:
<221> NAME/KEY: RB
<222> LOCATION: 1..25
<223> OTHER INFORMATION: right border sequence from the T-DNA of
      pGSV5
<220> FEATURE:
<221> NAME/KEY: MCS
<222> LOCATION: 26..75
<223> OTHER INFORMATION: multiple cloning site
<220> FEATURE:
<221> NAME/KEY: LB
<222> LOCATION: 76..100
<223> OTHER INFORMATION: left border sequence from the T-DNA of
      pGSV5

<400> SEQUENCE: 9

```
aattcaacg gtatatatcc tgccagtact cggccgtcga ccgcggtacc cggggaagct        60
tagatccatg gagccattta caattgaata tatcctgccg                            100
```

PATHOGEN-INDUCED PLANT PROMOTERS

BACKGROUND OF THE INVENTION (i) Field of the Invention

This invention pertains to new pathogen-induced promoters, particularly nematode-induced promoters, characterized by their selective induction of expression in the pathogen infection sites, particularly nematode infection sites of a plant. Provided in this invention are these new promoters, as well as chimeric gene constructs comprising these promoters as regulatory elements. Also provided herein are transgenic plants transformed to be less susceptible to nematode infection by the selectively induced expression of either a nematocidal toxin or a plant cell cytotoxic molecule upon nematode infection.

(ii) Description of Related Art

Plant-parasitic nematodes are small worm-like animals which feed on roots, stem or leaf tissues of living plants. They are present whenever plants are cultivated. Parasitic nematodes can cause significant plant yield losses, the most striking effect being a general reduction in plant growth. Often nematodes act as vectors for plant viruses. Plant diseases caused by nematodes include root galling, root lesions, root rot, stubby roots, stunting and wilting. In 1984, monetary losses, when all crops are considered, exceed US $ 100 billion annually (Sasser and Freckman, 1987). Ecto-parasitic nematodes, such as the dagger (Xiphinema spp.) nematodes, live outside the plant and pierce the plant cells with their stylet in order to feed. Migratory endoparasitic nematodes, such as the lesion (Pratylenchus spp.) nematodes, live and feed inside the plant, migrating through the plant tissues. Sedentary endoparasitic nematodes, such as the root-knot (Meloidogyne spp.) and cyst (Globodera spp. and Heterodera spp.) nematodes, live and feed either completely or partially inside the plant, inducing specialized fixed feeding sites called giant cells, syncytia or nurse cells in susceptible plants. Such fixed feeding sites serve as food transfer cells for the various developmental stages of the nematodes. Syncytia originate in the pericycle, endodermis or adjacent cortex (Jones. 1981).

Several methods were designed to obtain nematode resistant plants by expression of chimeric genes. One strategy involves the nematode induced expression of nematocidal products, particularly peptides or proteins, preferably at the site of nematode feeding. Other strategies were designed to eliminate the formation or reduce the metabolic activity of the nematode feeding structures, e.g. by selective destruction of the feeding structures through the expression of cytotoxic molecules in the plant under control of a nematode feeding site-selective promoter. In some applications, a molecule inactivating the cytotoxic molecule is expressed at low levels throughout the plant to prevent cell killing in other plant cells due to background expression (WO 92/21757, WO 93/10251).

To expand the applicability of the abovementioned strategies, new nematode-induced promoters with improved timing, selectivity, and strength, are continuously searched for (e.g. Goddijn et al., 1993).

WO 95/32288 describes nucleic acid sequences, isolated by subtractive cDNA library construction, which are preferentially expressed in feeding site cells.

WO 93/18170 describes in general terms the isolation of nematode-responsive promoters and the use thereof to provide root knot nematode resistance to plants.

WO 93/10251 describes a method for obtaining plants with reduced susceptibility to plant-parasitic nematodes by providing chimeric genes that disrupt or at least retard the formation of a nematode feeding structure.

WO 92/04453 describes a method of controlling nematodes, the method including the steps of identification of a gene induced within a successfully infected plant by nematode infection of said plant and modifying the gene to confer nematode resistance to the plant.

WO 92/15690 and U.S. Pat. No. 5,494813 are directed to methods of controlling plant parasitic nematodes using proteinase inhibitors.

WO 92/21757 provides nematode-responsive plant promoters, particularly useful in the production of transgenic plants which can produce fixed feeding site cells that become capable of killing, disabling or repelling nematodes or that are themselves killed or rendered unsuitable for nematodes to feed upon when nematodes infect the plants.

Gurr et al. (1991) describe a gene identified by a library screen with cDNA probes with an expression pattern that correlated with event in the immediate vicinity of the pathogen after syncytial establishment.

Goddijn et al. (1993) describe down regulation in the feeding structures of a number of viral and bacterial promoters which are highly active in non-infected roots, and also describe a number of transgenic plant lines obtained by interposon tagging, using a T-DNA with a promoterless uidA (gus) gene, with either downregulated or enhanced gus expression in nematode feeding sites.

Opperman et al. (1994) describe cis-acting sequences from the TobRB7 promoter mediating induction by the nematode, and report the exclusive expression in the developing feeding site of reporter genes driven by the nematode-responsive promoter sequences.

SUMMARY OF THE INVENTION

In accordance with the invention isolated DNA fragments are provided that comprise the nucleotide sequence of SEQ ID No. 5 from nucleotide position 1055 to 1417, or the nucleotide sequence of SEQ ID No. 4 from nucleotide position 46 to 408, particularly an isolated DNA fragment comprising the nucleotide sequence of SEQ ID No. 4 from nucleotide position 46 to 573, especially an isolated DNA fragment comprising the DNA sequence of SEQ ID No. 8, or variant isolated DNA fragments which comprise a nucleotide sequence which is essentially similar to one of the provided sequences, in particular which has 90% sequence similarity with the nucleotide sequence of SEQ ID No. 5 from nucleotide position 1055 to 1417 or which has 90% sequence similarity with the nucleotide sequence of SEQ ID No 4 from nucleotide position 46 to 408.

Also in accordance with the invention, isolated DNA fragments are provided, particularly an isolated DNA fragment comprising the DNA sequence of the about 528 bp Sspl-Pvull fragment of plasmid pARM1a (LMBP3638), an isolated DNA fragment comprising the DNA sequence of the about 3 kb Pstl-Styl fragment of plasmid pch/ARM1 D3500 (LMBP3635), an isolated DNA fragment comprising the about 1.3 kb Smal fragment of plasmid pARM1a1300 (LMBP3636), or an isolated DNA fragment comprising the about 3.7 kb Smal fragment of plasmid pARM1 a3500 (LMBP3637).

Further in accordance with the invention chimeric genes are provided, comprising the following operably linked DNA fragments:

a. a plant-expressible promoter comprising the isolated DNA fragments of this invention b. a foreign DNA region c. a 3' end formation and polyadenylation signal functional in plant cells.

Preferred chimeric genes of this invention are those, wherein the foreign DNA region encodes a proteinase inhibitor, or barnase. Further in accordance with this invention plant cells, plants and seeds comprising such chimeric genes are provided.

This invention further provides a method for preventing nematode-attack of a plant, comprising planting a plant harbouring an introduced foreign DNA which comprises any of the chimeric DNAs of this invention in a field susceptible to infection by nematodes; a method for combatting plant pathogens, particularly a root pathogen, which comprises expressing a foreign DNA in a plant under the control of a promoter comprising the cited DNA fragments, and the use of a promoter comprising the isolated DNA fragments of this invention to express a gene, i.e. produce a protein in fixed feeding sites or specialized root cells of a nematode infected plant.

DETAILED DESCRIPTION OF PREFERRED EMBODIMENT

Throughout the description and examples the following definitions apply:

"Nematode feeding cells" or "fixed feeding sites" should be understood as specialized feeding sites (such as giant cells, syncytia and nurse cells or hypertrophic cells and, if present, galls), the formation of which is induced by sedentary endoparasitic or semi-sedentary ectoparasitic nematodes in susceptible plants. The plant cells of such sites serve as food transfer cells for the various developmental stages of the nematodes.

"Nematode infected plant" means a plant in which a nematode has entered, either partially or entirely.

"Giant cells" should be understood as the multinucleate plant root cells induced by nematodes such as root-knot nematodes. The muitinucleate condition of each giant cell is believed to result from multiple mitoses in the absence of cytokinesis.

"Syncytium" refers to multinucleate plant root cells induced by nematodes such as cyst nematodes. The multinucleate condition of each syncytium results from cell wall dissolution between contiguous cells with preexisting nuclei.

"Nurse cells" refers to a group of six to ten uninucleated plant root cells, induced by nematodes such as e.g. Tylenchulus spp., which have a dense cytoplasm without a vacuole and a much enlarged nucleus and nucleolus.

"Galls" refers to a proliferation of cortical plant cells/tissue induced by nematodes. Typically, giant cells reside within galls.

"Nematode-induced promoter" means a promoter whose action in controlling transcription of a DNA sequence (e.g. gene) in a plant is induced (i.e., stimulated) upon infection of the plant by nematodes in specific cells of the plant's roots, particularly in cells of the plant's fixed feeding sites. A nematode-induced promoter when operably linked to a uidA gene, typically drives expression of β-glucuronidase in a plant infected by nematodes for two days, which can be visualized by histochemical GUS assays using 5-bromo4-chloro-3-indolyl-β-D-glucuronide as substrate, at least after 5 hours of incubation in the staining reaction.

"Promoter fragment" means a fragment of a promoter, particularly a nematode-induced promoter, that determines timing, selectivity or strength of the expression conferred by the promoter. A promoter fragment can comprise an autonomously functioning promoter or functions as a promoter, particularly a nematode-induced promoter when combined with other homologous or heterologous promoter fragments (such as e.g. a TATA box region). Nematode-induced promoters of the invention comprise at least one promoter fragment of the invention.

"Specific cells of a plant's root" or "specific root cells of a plant" means cells of a root tissue such as the fixed feeding sites, the pericycle, the endodermis, the cortex or the vascular tissue, preferably a) cells of the fixed feeding sites or b) cells of tissue (e.g., pericycle cells) which i) will differentiate into fixed feeding site cells upon infection of the plant by nematodes or ii) can be altered to reduce the ability of nematodes to feed at fixed feeding sites of the plant. Particularly preferred specific root cells of a plant are fixed feeding site cells.

"Expression" means transcription into an RNA product, post-transcriptional events and/or translation to a peptide or protein product from a DNA encoding that product, as well as possible post-translational events.

"Foreign" with regard to a DNA sequence, such as a first or second foreign a DNA of this invention, means that such a DNA is not in the same genomic environment (e.g. not operably linked to the same promoter and/or 3' end) in a plant cell, transformed with such a DNA in accordance with this invention, as is such DNA when it is naturally found in a cell of the plant, bacterium, animal, fungus, virus, or the like from which such a DNA originates.

"T1 (plants)" refer to the primary transformed plants regenerated from the primary transformed shoots. "S1 or T2 " refers to the second generation of plants germinated from seeds of self-fertilized T1 plants. "S2 or T3 plants" represent the third generation of transformed plants, grown from seeds obtained upon self-fertilization of T1 plants, etc.

Whenever it is stated that a sequence comprises the nucleotide sequence of SEQ ID No. X between nucleotide positions Y and Z, it is meant that the indicated sequence includes nucleotides Y and Z. Likewise, whenever it is stated that a sequence comprises the nucleotide sequence of SEQ ID No. X from nucleotide positions Y to Z, it is meant that the indicated sequence includes nucleotides Y and Z.

Methods to provide nematode-resistant plants comprising transformation of a plant by chimeric genes wherein a foreign DNA encoding an RNA and/or a protein or polypeptide, which when produced either kills, disables or repels nematodes or kills or at least disturbs significantly the metabolism, functioning and/or development of fixed feeding sites so as to limit further spread and reproduction of the nematode, preferably require the use of a promoter expressed in the nematode fixed feeding sites or specialized root cells of a plant, particularly a promoter that is induced in the nematode fixed feeding sites or specialized root cells of a plant upon nematode infection. Suitable nematode-induced promoters are induced early upon nematode infection, preferably early after the onset of nematode feeding which triggers the differentiation of fixed nematode feeding sites, particularly within two days after nematode infection.

One method to isolate suitable nematode-induced promoters relies on interposon tagging of plant genes whose expression is induced upon nematode infection. Interposon tagging allows random fusion of a promoterless reporter gene, such as the uidA gene, whose expression can be monitored, to (regulated) promoters. Nematode-infection of a collection of plants with randomly integrated interposons, and screening for glucuronidase expression allows selection of plant lines where reporter gene expression, preferably strong reporter gene expression is observed in the fixed feeding cells and where expression in uninfected plants is limited, preferably absent, and expression in cells other than the fixed feeding cells is limited, preferably absent.

A major advantage of interposon tagging strategy is that this monitoring of expression in cells other than fixed feeding sites can be done early in the screening procedure. A second advantage of the interposon tagging strategy is that the promoter with unknown sequence is identified by the adjacent presence of known sequences, allowing straight-forward isolation of the promoter. Several different interposons comprising a promoterless reporter gene for use in plants have been described [e.g. pΔgusBin19 (Topping et al., 1991), pGV1047 (Kertbundit et al., 1991), or pMOG553 (Goddijn et al., 1993). pGKB5 (Bouchez et al., 1993), pMNA2 (Mandal et al., 1995)].

A particularly preferred *Arabidopsis thaliana* line comprising a pΔgusBin19 T-DNA tagged, nematode-inducible promoter is line ARM1 and its progeny harbouring the T-DNA locus responsible for the observed gus expression pattern. The line ARM1 showed a very strong GUS-staining in the root galls on 2 to 4 days after inoculation with either *Heterodera schachtii* or *Meloidogyne incognita*. 7 days after infection, the staining intensity is less but still prominent, and 14 days after infection only very weak GUS-staining is found in the root galls. In addition, sites of lateral root initiation were stained, and some ARM1 plants exhibited GUS-staining in the vegetative shoot and regions of vascular tissue of roots and young leaves. Similar GUS-staining patterns as found with in vitro inoculation, were found upon soil inoculations. Gall-specific induction of gus expression after inoculation with a third nematode. *Xiphinema diversicaudatum*, was also observed. A cross section through a *X. diversicaudatum* gall induced on an ARM1 plant indicated that the reporter gene expression occurs in the multinucleate cells induced by the nematode. No GUS-activity was observed in either flowers, pollen or seeds of uninfected or infected ARM1 plants, nor was GUS-staining observed after mechanical injury in uninfected ARM1 plants. Addition of hormones to roots, e.g. by incubating roots on a callus induction medium (Valvekens et al., 1991) resulted in a GUS-positive response in the root vascular tissue regions abutting the protruding calli, and in the root tips.

Segregation-analysis of ARM1 seeds on kanamycin-containing medium allowed to deduce the presence of only one T-DNA tagged locus. By Southern analysis it was determined that two intact T-DNA copies were present in reverse direction with the two right borders linked together and that a third incomplete T-DNA copy, integrated at a different locus was present. The T-DNA copy at the second locus does not comprise an nptII gene and segregates independently from the first locus which is responsible for the characteristic gus expression pattern described above.

A particularly preferred nematode-induced promoter, is the promoter tagged as by the insertion of the T-DNA in Arabidopsis thaliana line ARM1, and obtainable from genomic DNA from an ARM1 plant by isolation of the DNA region upstream of the uidA gene at the tagged locus. This promoter can be isolated by a variety of methods, such as isolation of a clone of the T-DNA left border/plant DNA junction fragment by constructing a representative clone library of the DNA of *A. thaliana* line ARM1 in a plasmid or phage cloning vector, followed by screening of the library using a labelled DNA fragment comprising the T-DNA left border. However, a more straight-forward and particularly preferred method is the inverse PCR (iPCR). In inverse PCR the knowledge of the sequence of the T-DNA tag, particularly of the left border of the T-DNA, allows the isolation of the immediately adjacent unknown plant-derived sequences, particularly those immediately adjacent to the T-DNA left border. To this end, suitablesized fragments are preferably identified by restriction enzyme digestion of ARM1-derived DNA, followed by Southern-type hybridization to a labelled fragment comprising the nucleotide sequences of the T-DNA used for tagging (e.g. pΔgusBin19) adjacent to the left border. Suitable restriction enzymes should a preferably have at least one recognition site in the known sequence, thus generating a DNA fragment that consists partially of known sequences, flanked by unknown sequences. In one embodiment of the invention using plant line ARM1, the T-DNA locus responsible for the specific GUS- pattern observed comprises two T-DNA copies in inverted repeat over the right border, hence two possible left border/plant DNA junction fragments, designated ARM1a and ARM1b can be isolated. Preferred enzymes for ARM1 left border isolation by iPCR are SspI and EcoRI which generate suitably sized fragments for isolation of ARM1a and ARM1b respectively. In the next step, the restricted DNA is ligated under circumstances that allow preferentially circularization by standard methods, and this self-ligated DNA is subsequently used as template in a standard PCR reaction. Suitable primers for the iPCR reaction should preferably be complementary at one hand to the known sequence adjacent to the restriction site used to digest the DNA, and on the other hand to the known sequence adjacent to the junction site of known and unknown sequence. Both primers should be facing outwards, i.e. the primers should be complementary to opposite DNA strands and upon hybridization with a linear double stranded DNA fragment comprising the nucleotide sequences complementary to the sequences of the primer, the nucleotide sequence between the 3' ends of the primers should be larger than the nucleotide sequence between the 5' ends of the primers. Preferred primer combinations are the primers having the sequence of SEQ ID No. 1 and SEQ ID No. 2 for isolation of ARM1a, and the primers having the sequence of SEQ ID No. 1 and SEQ ID No. 3 for isolation of ARM1b. Although theoretically, the same set of primers should amplify both junction fragments of ARM1, the preferential amplification of smaller fragments by PCR allows isolation of only the smallest fragment. SspI digested, self-ligated ARM1 DNA thus allows isolation of the ARM1a T-DNA/plant DNA junction, while EcoRI digested, self-ligated ARM1 DNA thus allows isolation of the ARM1b T-DNA/plant DNA junction. These PCR amplified T-DNA plant DNA junction fragments can be cloned, e.g., taking advantage of the non-template-dependent addition of a single deoxyadenosine to the 3' end of PCR products by many thermostable polymerases, in a vector cleaved with a blunt end enzyme to which a 3' terminal thymidine was added to both ends (U.S. Pat. No. 4,766,072), and their nucleotide sequence determined (e.g. as represented in SEQ ID No. 4).

In a preferred embodiment of the invention the PCR amplified fragments are used as a probe to screen a genomic library of DNA of a wild-type *A. thaliana* line to isolate the genomic clones (such as ch/ARM1A, ch/ARM1B, ch/ARM1C or ch/ARM1D), carrying the uninterrupted genomic DNA of the wild-type line C24 which is the target sequence for T-DNA integration in line ARM1. Determination of the nucleotide sequence of the isolated genomic DNA can be used to design novel primers (such as MAKAR17: SEQ ID No. 7) that in combination with a primer having a nucleotide sequence complementary to the left end of the T-DNA of pΔgusBin19 (such as MAKAR4. SEQ ID No. 6) can be used to amplify by PCR specifically the T-DNA/plant DNA border fragment without having to resort to iPCR, such as e.g. the fragment amplified using primers MAKAR4 and MAKAR17, the nucleotide sequence of which is represented in SEQ ID No. 8.

Furthermore, this genomic DNA can be used to isolate transcription regulating sequences, located further upstream in case the amplified fragments are too small to contain all required transcription regulating fragments. For convenience of DNA-manipulation it is preferred that fragments of the genomic phage clones are subcloned in conventional cloning vectors, such as e.g. the 3.5 kb XbaI genomic DNA fragment of ch/ARM1D (wherein T-DNA insertion occurred in the line ARM1) in vector pbluescript KS, yielding the plasmid chARM1D3500.

Isolated sequences from the PCR-fragments or sequences from the corresponding genomic clones are subsequently cloned in front of a promoterless reporter gene to identify the regions required from nematode-induced promoter activity. Only sequences comprising the plant sequences from ARM1a are active in promoting transcription in fixed feeding sites upon nematode induction.

The promoter can be further analysed to identify regions that confer more specific and/or more enhanced promoter activity when combined with either homologous or heterologous transcription signals such as TATA-boxes or upstream enhancing elements. It was found that an SspI-PvuII fragment of ARM1a comprising about 390 bp of plant-derived nucleotide sequence (comprising the nucleotide sequence of SEQ ID No. 4 from nucleotide position 46 to 408, which essentially corresponds to the nucleotide sequence of SEQ ID No. 5 from nucleotide position 1055 to 1417) conferred nematode-induced expression of a promoterless reporter gene (uidA) in the fixed feeding site in a transgenic line comprising this chimeric gene with the same timing as observed in line ARM1. However, no GUS-staining was observed in cells other than the fixed feeding cells. It is therefore expected that promoters comprising the nucleotide sequence of SEQ ID No. 4 from nucleotide position 46 to 408 or the nucleotide sequence of SEQ ID No. 5 from nucleotide position 1055 to 1417, promote a specific transcription in fixed feeding cells or specific root cells of a plant upon nematode infection. Clearly, the enhanced specificity of these promoters, makes them even more suited for use in the construction of chimeric genes to develop nematode-resistant plants. The observed gus expression upon nematode infection in the transgenic plant comprising the chimeric reporter gene described above, was however weaker than that observed in the line ARM1 upon nematode infection. A promoter comprising about 100 additional nucleotides of the upstream sequences (as comprised on plasmid pARM1a1300 and having the nucleotide sequence of SEQ ID No. 8 from 1 to 1190, comprising a sequence corresponding essentially to the sequence of SEQ ID No. 5 from 945 to 1444) was found to drive a similar gus expression pattern as that described above for the SspI-PvuII fragment of ARM1a.

Inclusion of about 2.7 kb upstream genomic DNA sequence into the latter described promoter by exchange of the about 0.4 kb PstI/StyI fragment for the about 3 kb PstI/StyI fragment of ch/ARM1D3500, (yielding plasmid pARM1a3500) resulted in similar timing, pattern and level of gus expression in a transgenic plant comprising the chimeric gene with the larger promoter infected by nematodes, as observed in ARM1 infected by nematodes. It is therefore expected that the about 2.7 kb upstream genomic DNA sequence comprises a transcription enhancing sequence.

It is expected that further dissection of the smallest promoter fragment will lead to the identification of specific DNA sequences that when comprised within a promoter region will yield nematode-specific promoters with enhanced selectivity and/or expression. Particularly interesting for this purpose are those DNA sequences from the smallest nematode-induced promoter, which exhibit structural features such as repeats or stem-loop regions i.e. the nucleotide sequences of SEQ ID No. 5 between nucleotides 996 and 1018, 923 and 946, 1001 and 1021, 1016 and 1029, 1004 and 1059, 1250 and 1292, 1356 and 1388, 1375 and 1432 (stem-loop structures) and the nucleotide sequences of SEQ ID No. 5 between nucleotides 849 and 864, 1055 and 1070, 996 and 1009, 1019 and 1032, 849 and 858, 1055 and 1064, 1011 and 1025, 1246 and 1260, 1242 and 1252, 1274 and 1284, 1356 and 1365, 1386 and 1395 (repeats)

A preferred nematode-induced promoter comprises the nucleotide sequence of SEQ ID No. 5 from nucleotide position 1055 to 1417. Another preferred nematode-induced promoter comprises the nucleotide sequence of SEQ ID No. 4 from nucleotide position 46 to 408. A particularly preferred promoter fragment is a DNA fragment comprising the nucleotide sequence of SEQ ID No. 4 from nucleotide position 46 to 573. Yet another particularly preferred promoter fragment is a DNA fragment comprising the DNA sequence of the 528 bp SspI-PvuII fragment of pARM1a. An especially preferred nematode-induced promoter comprises the about 1.3 kb SmaI fragment of pARM1a1300.

A preferred nematode-induced promoter fragment comprising the upstream enhancing sequence is a promoter fragment comprising the DNA sequence of the about 3 kb PstI-StyI fragment of Ch/ARM1D3500. particularly a DNA fragment comprising the DNA sequence of the about 3.7 kb SmaI fragment of pARM1a3500. Another preferred nematode-induced promoter fragment comprising the upstream enhancing sequence is a promoter fragment comprising the DNA sequence of the about 3 kb PstI-StyI fragment of pARM1a3500, particularly an isolated DNA fragment comprising the DNA sequence of the about 3 kb PstI-StyI fragment of ch/ARM1 D3500 and the DNA sequence of SEQ ID No. 8 from position 367 to 1190.

Variant promoter fragments can be obtained or can be derived from the promoter fragment which still will have the specificity in timing and pattern of gus expression as the original sequences. Such modifications include exchange of a nucleotide for another nucleotide, insertions or deletions of a limited number of nucleotides, preferably not more than three nucleotides, particularly not more than two nucleotides, inversions of a limited number of nucleotides and the like. Particular nucleotide positions which can be varied include but are not limited to, the nucleotides at positions 1072, 1152, 1229 or 1352 of SEQ ID No. 5. These variant promoter fragments have essentially a similar DNA sequence as the promoter fragments comprising the nucleotide sequence of SEQ ID No. 4 from nucleotide position 46 to 408 and have a conserved timing and pattern of the induction of the promoter by nematode infection.

Promoters with essentially similar sequences as the described nematode-inducible promoters, which have comparable or identical characteristics in terms of kinetics or pattern of induction by nematode infection, can be isolated from other plant species using the promoters described in this invention, as a hybridization probe under conventional hybridization conditions, preferably stringent hybridization conditions. Alternatively, the nucleotide sequence of the promoter fragments provided in this invention can be used to design appropriate PCR primers to be used to isolate promoter fragments with essentially similar sequences from other plant species by PCR-based techniques. Designing appropriate oligonucleotides to be used as primers for PCR is well known by the skilled artisan. It is preferred that such oligonucleotides comprise a contiguous sequence of at least 30 nucleotides, particularly 50 nucleotides which are identical or complementary to the provided sequences such as the nucleotide sequence of SEQ ID No. 5 from nucleotide position 1 to 1444. Furthermore it is expected that variant promoter fragments will comprise a contiguous nucleotide sequence of 30 nucleotides, particularly 50 nucleotides, which is identical to a 30 nucleotide sequence, particularly a 50 nucleotide sequence of SEQ ID No 4 from nucleotide position 46 to 408.

With regard to nucleotide sequences (DNA or RNA), such as sequences of regulatory regions of a gene. "essentially similar" means that when two sequences are aligned, the percent sequence identity -i.e., the number of positions with identical nucleotides divided by the number of nucleotides in the shorter of the two sequences-is higher than 80%, preferably higher than 90%, particularly higher than 95% especially with regard to regulatory regions. The alignment of the two nucleotide sequences is performed by the Wilbur and Lipmann algorithm (Wilbur and Lipmann, 1983) using a window-size of 20 nucleotides, a word length of 4 nucleotides, and a gap penalty of 4. Computer-assisted analysis and interpretation of sequence data, including sequence alignment as described above, can be conveniently performed using the programs of the lntelligenetics™ Suite (Intelligenetics Inc., CA).

The chimeric genes of the invention using the promoters or the promoter fragments provided in the invention will be useful in other plant species to obtain resistance to nematode infection. Preferred host plants for the nematode-inducible chimeric genes of the invention are potato plants, particularly potatoes grown for starch production, and oilseed rape plants. Other preferred host plants for the nematode-inducible chimeric genes of the invention are soybean. Beta spp, cereals (e.g. wheat, corn, rice and barley), carrots, tomato, tobacco, *Pisum sativa,* or Vicia species.

It is expected that induction of the promoters described will also occur upon infection of the plant by other plant parasitic nematodes such as *Meloidogyne hapla, M. exigua, M. indica, M. javanica, M. africana, M. graminis, M. graminicola, M. arenaria, M. chitwoodii, Heterodera mexicana, H. punctata, H. cajani, H. glycines, H. oryzae, H. trifolii, H. avenae, H. carotae, H. cruciferae, H. goetingiana, Globodera rostochiensis, G. pallida, G. tabacum* in addition to the species already mentioned. Furthermore it is believed that induction of the promoters described will occur upon infection of the plant by migratory nematodes inducing feeding cell development, such as nematodes selected from the genera Xiphinema, Nacobus, Longidorus.

It is known that expression driven by pathogen-responsive promoter regions can often be influenced by more than one pathogen or pest (Strittmatter et al., 1996). The presently identified promoters can thus be used for other purposes than the ones described above, e.g., to obtain enhanced resistance of a plant to other pathogens or pests in accordance with this invention whenever infection of those pathogens or pests triggers enhanced or selective transcription from the promoters provided in the invention. Examples of such other pathogens include fungi, viruses, and bacteria which are able to induce the promoter at their site of infection of the plant.

In one embodiment of this invention, the provided nematode-induced promoters are used to express a foreign gene predominantly, preferably selectively in fixed feeding site cells, or specialized root cells of a plant. In a preferred embodiment the expressed foreign DNA encodes a polypeptide or protein which can kill or disable nematodes: toxins from the *Bacillus thuringiensis* isolates described in EP 303426, collagenases, chitinases, glucanases, peroxidases, superoxide dismutases, lectins, glycosidases, antibacterial peptides (e.g. magainins, cecropins and apidaecins), gelatinases, enzyme inhibitors, particularly proteinase-inhibitors such as members of the Bowman-Birk, Kunitz, potato 1 potato 2, cucurbit, cystatin families of proteinase-inhibitors, as described in U.S. Pat. No. 5,494,813, or neurotoxins. It is preferred, particularly where the plant is a food plant, that the polypeptide be non-toxic to animals, and particularly be non-toxic to humans.

In another embodiment of the invention, the promoters of the invention are used to express a foreign DNA sequence encoding an RNA, polypeptide or protein that when expressed in the cell of a plant, particularly a cell of a fixed feeding site will disable in such a plant cell, metabolic activities that are essential for the feeding and survival of the feeding nematodes. Examples of such first foreign DNA sequence encoding an RNA are antisense DNAs encoding RNAs complementary to genes encoding products essential for the metabolism, functioning and/or development of the fixed feeding sites or DNAs encoding ribozymes targeted towards the mentioned genes. In a particularly preferred embodiment, the promoters of the invention are used to express an antisense RNA or ribozyme directed towards mRNA coding for hydroxy-methyl-glutaryl CoA reductase (HMGR). HMGR is a rate-limiting enzyme for the production of a large number of compounds such as terpenes and sterols. As plant pathogenic nematodes are unable to synthesize their own sterols (Chitwood and Lusby, 1991) they are entirely dependent on the plant supply; down regulation of this enzyme in fixed feeding site cells, will have severe effects on the development of the nematode.

In a preferred aspect of the invention, the provided nematode-induced promoters are used to transcribe a DNA region encoding a protein or polypeptide which, when produced in a plant cell, such as a cell of a fixed feeding site, kills such cell or at least interferes substantially with its metabolism, functioning or development. Examples of such transcribed DNA regions are those comprising DNA sequences encoding ribonucleases such as RNase T1 and especially barnase (which degrades RNA molecules by hydrolysing the phosphodiester bound after any guanine residue; Hartley, 1988); cytotoxins such as the A-omain of diphtheria toxin [Greenland et al., 1983) or the Pseudomonas exotoxin A. Several other DNA sequences encoding proteins with cytotoxic properties can be used in accordance with their known biological properties. Examples include, but are not limited to, DNA sequences encoding proteases such as papain: glucanases; lipases such as phospholipase A2; lipid peroxidases; methylases such as the *E. Coli* Dam methylase: DNases such as the EcoRI endonuclease: plant cell wall inhibitors, enzymes which catalyze the synthesis of phytohormones of gene 1 and gene 2 of the T-DNA of Agrobacterium.

Other examples of foreign DNA sequences which can be expressed under control of the nematode-induced promoters of the invention to inhibit the development of fixed feeding cells are DNA sequences encoding antibodies immunoreactive with molecules in the plant cells (e.g. proteins, carbohydrates and nucleic acids necessary for the development of the feeding cells including but not limited to, RNA polymerase, respiratory enzymes, cytochrome oxidase. Krebs cycle enzymes, protein kinases, enzymes involved in the shikimic acid pathway) or with nematode-specific molecules such as compounds secreted through the nematode's feeding stylet that initiate or maintain feeding cells. As used herein, "antibody" refers to a variety of forms of immunoglobulin molecules besides whole antibodies, including for example. Fv, Fab, and F(ab)$_2$ fragments, single chain antibodies and the like.

Alternatively, the first foreign DNA operably linked to the nematode-induced promoters of the invention encodes an enzyme transforming an otherwise harmless substance into a cytotoxic product, such as the N-acetyl phosphinotricin-deacetylase, transforming unoxious N-acetyl phosphinotricin into the herbicide phosphinotricin, in the cells of the fixed feeding site, thus impairing the development of a fixed feeding site cell upon spraying with N-acetyl phosphinotricin (EP 0 531 716).

When a cytotoxic protein or a protein generating cytotoxic substances is expressed under control of the nematode-induced promoters of the invention, it is preferred to have a second foreign DNA, encoding an RNA and/or protein or peptide inhibiting or reversing the cytotoxic effect of the first foreign DNA gene product, expressed throughout the plant, preferably in all cells other than those infected by the nematode, to prevent any detrimental effects on yield or performance of the plant in the field under diverse conditions.

In accordance with the invention, the second foreign DNA, controlled by a second promoter, encodes a second RNA and/or protein or polypeptide which, when produced or overproduced in cells of a plant, inhibits or preferably inactivates the first RNA, protein or polypeptide in such cells. Second foreign DNAs preferably encode, for example, the following: barstar which neutralizes the activity of barnase; EcoRI methylase which prevents the activity of the endonuclease EcoRI, or a protease inhibitor neutralizing the activity of a protease, such as papain (e.g. papain zymogen and papain active protein). Another preferred example of a second foreign DNA is a DNA which encodes a strand of antisense RNA which would be complementary to a strand of sense first RNA.

Similarly, expression of a molecule negatively affecting the plant cell's metabolism is preferably countered by an inhibitor molecule, such as a DNA encoding an antisense RNA molecule or a ribozyme, to prevent any detrimental effect on yield or performance of the plant by leaky expression.

Preferably this second foreign DNA is under the control of a promoter whose expression is constitutive or down-regulated upon nematode infection at the site of nematode-infection, such as the CaMV35S promoter (Benfey and Chua. 1990) or the promoter of the nopaiine synthase gene of *Agrobacterium tumefaciens* T-DNA (Depicker et al., 1982) or any of the promoters which are down-regulated by nematode infection as described in Goddijn et al. (1993) and WO92/21757.

In a particularly preferred embodiment the first foreign DNA operably linked to the nematode-induced promoters of the invention encodes a barnase protein as described in PCT publication WO92/09696. Preferably, together with such a chimeric gene, a second chimeric gene expressing the barstar protein (Hartley, 1988) is expressed in the same plant.

In plants, the second chimeric gene is preferably in the same genetic locus as the nematode-inducible chimeric gene so as to ensure their joint segregation. This can be obtained by combining both chimeric genes on a single transforming DNA, such as a vector or as part of the same T-DNA. However, in some cases a joint segregation is not always desirable. Therefore both constructs can be present on separate transforming DNAs, so that transformation might result in the integration of the two constructs at a different location in the plant genome.

The newly isolated promoters have specific advantages over the currently available nematode-induced promoters in their enhanced specificity and the time of induction. Indeed, a promoter induced early after nematode-infection with only limited background in the lateral root initiation site is ideally suited to drive expression of a coding region encoding a cytotoxic or nematotoxic protein at the site of nematode-infection.

The chimeric genes comprising the isolated promoter fragments of this invention preferably also comprise a 3' untranslated region, which directs correct polyadenylation of mRNA and transcription termination in plant cells. These signals can be obtained from plant genes such as polygalacturonase genes, or they can be obtained from genes that are foreign to the plants. Examples of foreign 3' transcription termination and polyadenylation signals are those of the octopine synthase gene (De Greve et al., 1982), of the nopaline synthase gene (Depicker et al, 1982) or of the T-DNA gene 7 (Velten and Schell, 1985) and the like.

Preferably, the recombinant DNA comprising the nematode-inducible chimeric gene also comprises a conventional chimeric marker gene. The chimeric marker gene can comprise a marker DNA that is under the control of, and operatively linked at its 5' end to, a plant-expressible promoter, preferably a constitutive promoter, such as the CaMV 35S promoter, or a light inducible promoter such as the promoter of the gene encoding the small subunit of Rubisco; and operatively linked at its 3' end to suitable plant transcription termination and polyadenylation signals. The marker DNA preferably encodes an RNA, protein or polypeptide which, when expressed in the cells of a plant, allows such cells to be readily separated from those cells in which the marker DNA is not expressed. The choice of the marker DNA is not critical, and any suitable marker DNA can be selected in a well known manner. For example, a marker DNA can encode a protein that provides a distinguishable color to the transformed plant cell, such as the A1 gene (Meyer et al., 1987), or can provide herbicide resistance to the transformed plant cell, such as the bar gene, encoding resistance to phosphinothricin (EP 0,242,246), or can provide antibiotic resistance to the transformed cells, such as the aac(6') gene, encoding resistance to gentamycin (WO94/01560).

In still a further embodiment of the present invention, a plant with increased nematode resistance can be obtained from a single plant cell by transforming the cell in a known manner, resulting in the stable incorporation of a nematode-inducible gene of the invention into the nuclear genome.

A recombinant DNA comprising a chimeric gene of this invention can be stably incorporated in the nuclear genome of a cell of a plant, particularly a plant that is susceptible to Agrobacterium-mediated transformation. Gene transfer can be carried out with a vector that is a disarmed T1-plasmid, comprising a nematode induced chimeric gene of the invention, and carried by Agrobacterium. This transformation can be carried out using the procedures described, for example, in EP 0/116,718. Ti-plasmid vector systems comprise a foreign DNA under control of the nematode-induced promoters of the invention gene between the T-DNA border sequences, or at least to the left of the right T-DNA border. Alternatively, any other type of vector can be used to transform the plant cell, applying methods such as direct gene transfer (as described, for example, in EP 0,233,247), pollen-mediated transformation (as described, for example, in EP 0,270,356. WO85/01856 and U.S. Pat. No. 4,684,611), plant RNA virus-mediated transformation (as described, for example, in EP 0,067,553 and U.S. Pat. No. 4,407,956), liposome-mediated transformation (as described, for example, in U.S. Pat. No. 4,536,475), and the like.

Cells of monocotyledonous plants, such as the major cereals, can also be transformed using wounded or enzyme-degraded immature embryos, or wounded or enzyme-degraded compact embryogenic callus, as described in WO92/09696. The resulting transformed plant cell can then be used to regenerate a transformed plant in a conventional manner. For corn, other methods such as microprojectile bombardment of Type II callus as described, for example, by Fromm et al.(1990) and Gordon-Kamm et al. (1990) are suitable as well.

The obtained transformed plant can be used in a conventional breeding scheme to produce more transformed plants with the same characteristics or to introduce the nematode-inducible chimeric gene of the invention in other varieties of the same or related plant species. Seeds obtained from the transformed plants contain the chimeric gene comprising the nematode-induced promoters of the invention as a stable genomic insert.

The following Examples describe the isolation and characterization of nematode-inducible promoters and promoter fragments from *Arabidopsis thaliana* and the use of such a promoter for the modification of nematode-resistance properties in plants. Unless stated otherwise in the Examples, all recombinant DNA techniques are carried out according to standard protocols as described in Sambrook et al. (1989) *Molecular Cloning: A Laboratory Manual*. Second Edition. Cold Spring Harbor Laboratory Press, NY and in Volumes 1 and 2 of Ausubel et al., (1994) *Current Protocols in Molecular Biology, Current Protocols*, USA. Standard materials and methods for plant molecular work are described in *Plant Molecular Biology Labfax* (1993) by R. D. D. Croy, jointly published by BIOS Scientific Publications Ltd (UK) and Blackwell Scientific Publications, UK.

In the examples and in the description of the invention, reference is made to the following sequences of the Sequence Listing:

| | |
|---|---|
| SEQ ID No. 1: | nucleotide sequence of primer 1 |
| SEQ ID No. 2: | nucleotide sequence of primer 2 |
| SEQ ID No. 3: | nucleotide sequence of primer 3 |
| SEQ ID No. 4: | nucleotide sequence of the PCR fragment ARM1a |
| SEQ ID No. 5: | nucleotide sequence of the genomic clone of the T-DNA insertion site in ARM1. comprising the promoter region |
| SEQ ID No. 6: | nucleotide sequence of the oligonucleotide MAKAR 4 |
| SEQ ID No. 7: | nucleotide sequence of the oligonucleotide MAKAR 17 |
| SEQ ID No. 8: | nucleotide sequence of the PCR amplified fragment using primers MAKAR 4 and MAKAR 17 |
| SEQ ID No. 9: | T-DNA of pGSV5 |

EXAMPLES

Example I

T-DNA tagging leading to the identification of a promoter induced by nematode inoculation in an early stage.

1.1 Transformation procedure

For the T-DNA tagging of *Arabidopsis thaliana*. pΔgusBin19 (Topping et a/., 1991) was used. The nucleotide sequence of the T-DNA of pΔgusBin19 is available from the EMBL database under the Accession Number U12638, and is herein incorporated by reference, pΔgusBin19 comprises at the left border a promoterless uidA gene, followed by the 3' end formation and poly-adenylation signal of the nos gene: the selection marker (nptll) is under control of the nos promoter and 3' end formation and poly-adenylation signal. Upon integration of the T-DNA downstream of a plant-promoter region, the promoterless uidA gene can be expressed, resulting in detectable β-glucuronidase activity.

pΔgusBin19 was introduced into the Agrobacterium strain C58C1Ri$^R$ (Holsters et al., 1980) harbouring either pGV2260 (Deblaere et al., 1985) or pMP90 (Koncz and Schell. 1986).

All transformations were carried out by Agrobacterium inoculation of *Arabidopsis thaliana* (ecotype C24) root tissue according to the method described by Clarke et al. (1992), or to a modified version of that protocol described by Barthels et al. (1994) or Karimi et al. (1994) wherein, callus-inducing medium (CIM) and shoot inducing medium (SIM) were supplemented with plant hormones as described by Valvekens et al. (1988) or by Marton and Browse (1991). Agrobacterium growth was prevented by adding 500 mg/l triacilline (SKB) or 850 mg/l vancomycin to the SIM in combination with a shoot overlay medium containing 850 mg/l vancomycin or 100 mg/l timentin (DUCHEFA) respectively. Shoots were transferred to 50 ml conical tubes containing 15 ml root inducing medium to promote root development. The root inducing medium is the germination medium described by Valvekens et al. (1988) to which 1 mg/l indole-3-butyric acid was added. Seeds were harvested under sterile conditions and sown on germination medium containing 50 mg/l kanamycin monosulfate. Plates were kept at 4° C. for 2 to 3 days prior to incubation in a growth chamber at 22° C. with a light regime of 16 hrs light followed by 8 hrs darkness. In this way 1874 lines of seed (S1) were generated, of which upon further analysis. 22% did either not germinate or were Km$^5$.

1.2. Screening strategy

The resulting transformed plants were analysed for nematode-induced gus expression patterns in the following way.

In vitro inoculations with *Heterodera schachtii* or *Meloidogyne incognita*, to detect specific gus expression at the nematode infection places and feeding sites, were performed on T3 plants. S2 seeds were surface sterilized by treatment with 70% ethanol for 2 min followed by immersion in a 5% sodium hypochlorite solution for 15 min and germinated on the germination medium described by Valvekens et al., 1988 supplemented with 50 mg/l kanamycin monosulfate. Two week old seedlings were transferred to a Petri dish containing a thin layer of Knop medium (Sijmons et al., 1991). The Petri dishes were incubated slightly tilted (to promote uni-directional root growth) at 22° C. (16 hr light/8 hr dark cycle) for two days. The roots were then inoculated by second stage juveniles from *H. schachtii* or *M. incognita* hatched for 5–7 days before, at an average density of 20 larvae per root system. Infections were allowed to proceed under the same tissue culture conditions. Four to six days post-inoculation, the plants were examined for β-glucuronidase activity. Nematodes used for the inoculation were cultured in the following way. *Meloidogyne incognita* cultures were maintained in vitro on *Lycopersicon esculentum* hairy roots which are cultured continuously on hormone free Gamborg's B5 medium (Flow Laboratories, Bioggio Switzerland) supplemented with 2% sucrose and 1.5% Difco Bacto agar. *H. schachtii* was grown in vitro on *Sinapis alba* roots on Knop medium (Sijmons et al., 1991). Hatching was stimulated by putting the cysts (for *H. schachtii*) or the galls (for *M. incognita*) on 70 μm Nylon Sieves (Falcon 2350 Cell strainer Becton Dickinson, Bedford, Mass.) submerged in filter-sterile root exudate from *Brassica napus* or sterile de-ionized water, respectively.

Histochemical localization of β-glucuronidase activity was performed using the substrate 5-bromo4-chloro-3-indolyl glucuronide (X-glu: Europa Research Products Ely, U.K.) according to Jefferson (1987) with the following modifications. 50 μl X-Glu (20 mg/ml in N,N-dimethyl formamide) was diluted to a final concentration of 2 mM in 1 ml of a 0.1 M sodium phosphate buffer pH7.2. Oxidative dimerization of the produced indoxyl residues was enhanced by adding potassium ferricyanide/ferrocyanide to a final concentration of 0.5 mM. Incubation of whole plantlets in phosphate buffer was preceded by a short treatment (15 to 30 min) with 90% ice-cold acetone followed by several washes with 0.1 M sodium phosphate pH7.2. The GUS-reaction was allowed to proceed from 6 hours to overnight at 37° C. Stained tissues were subsequently fixed for few hours to overnight in 2.5% glutaraldehyde (AGAR Scientific LTD., Stansted, U.K.) at 4° C. to prevent dilution of the GUS-product. To remove all pigments and brown phenolics, the stained material was incubated in chlorallactophenol (CLP: 2:1:1 mixture of chloral hydrate, lactic acid and phenol: Beeckman and Engler, 1994). The resulting translucent plant material was monitored for gus expression pattern using a light microscope. This material could be further stained to visualize nematodes inside the root tissues, by incubating in acid fuchsin dye during 16 hr and subsequently destaining in a saturated chloral hydrate solution.

In this way 284 transgenic lines were analysed, of which the line designated ARM1 had a very interesting expression pattern, warranting further detailed analysis.

1.3. Phenotypic analysis of the ARM1 line

The line ARM1 showed a very strong GUS-staining in the root galls on 4 days after inoculation with either *H. schachtii* or *M. incognita*. 7 days after infection the staining intensity is less but still prominent, and 14 days after infection only very weak GUS-staining is found in the root galls. GUS-staining of the fixed feeding sites of plants 4 days after inoculation, was observed as soon as half an hour after the onset of the GUS-staining reaction, and very prominent 1 to 2 hr after starting the GUS-reaction. Upon cross section of ARM1 galls, a very strong and uniform staining with the dye concentrated in the giant cells was observed.

In addition, after overnight incubation, sites of lateral root initiation were stained, and some ARM1 plants exhibited GUS-staining in the vegetative shoot and regions of vascular tissue of roots and young leaves.

To verify these results under conditions mimicking more closely the natural situation, ARM1 plants were inoculated in soil. Therefore, two weeks old *A. thaliana* seedlings were transferred to a 1:2 mixture of cutting soil and potting soil in open translucent plastic tubes. Forcing the roots to grow along one side of the tube, achieved by placing these slanting in rectangular flower-boxes, permitted more controlled inoculations and reproducible infections (Klap and Sijmons. 1994). Inoculations were performed after 2 more weeks of growth at 22° C. and 16 hours light by injecting a suspension containing 250 second stage juveniles (5 to 7 days post hatching) of *H. schachtii* or *M. incognita* in 1.5 ml H₂O per root system. One to 2 weeks later, plants were carefully washed and stained for GUS. Similar GUS-staining patterns as found with in vitro inoculation, were found upon soil inoculations. Gall-specific induction of gus expression after inoculation with a third nematode. *Xiphinema diversicaudatum*, was also observed. This result is especially interesting in the light of the different infection mode of *X. diversicaudatum*. Despite its ectoparasitic nature, this nematode feeds for longer periods and can be regarded as being semi-sedentary. *X. diversicaudatum* infection also leads to the development of galls. *X. diversicaudatum* was cultured in vivo on raspberry. Its size permits easy isolation from the sand through sieving. *X. diversicaudatum* inoculations in soil were performed in the following way. Seven to ten *A. thaliana* seeds were sown in a 1:1 sand:compost mixture in 30 ml plastic pots and grown for 14 days. Pots were inoculated twice with 5 to 10 *X. diversicaudatum* nematodes, with an interval of one week. One week after the last inoculation, roots were washed and stained for GUS-activity. A cross section through a *X. diversicaudatum* gall induced on an ARM1 plant indicated that the reporter gene expression occurs in the multinucleate cells induced at the nematode penetration site.

No GUS-activity was observed in either flowers, pollen or seeds of uninfected or infected ARM1 plants, nor was GUS-staining observed after mechanical injury in uninfected plants.

Expression of the gus gene was also monitored after 6 days of incubation of roots of two week old ARM1 plants on callus inducing medium (Valvekens et al.. 1991). A GUS-positive response was observed in the root vascular tissue regions abutting the protruding calli, and in the root tips.

1.4 Inoculation time-course experiments.

All inoculation time course experiments were performed in vitro on Knop medium containing 1% sucrose, using *H. schachtii*. For each line, several Petri dishes (9 cm diameter) were prepared with 20 seeds lined up in two rows, which had been vernalized at 4° C. for 3 days. Ten days after germination, each plant was inoculated with 30 second stage juveniles. Plants were monitored for GUS-activity at 2, 4, 7, 12 and 30 days post-inoculation (dpi). The GUS-assays were performed on the infected plants in the Petri dish. To this end, 4 ml X-glu solution including Fe-cyanide was poured on top of the agar, and the plates were incubated at 37° C. for 24 hr. Subsequently, plants were examined for GUS-activity in the nematode feeding structures. Scores of a particular time point are the average value of several counts of GUS-positive NFS (irrespective the GUS-activity level).

| | % syncytia with GUS-activity | | | | |
|---|---|---|---|---|---|
| | 2 dpi | 4 dpi | 7 dpi | 12 dpi | 30 dpi |
| ARM1 | 92.9 | 80.5 | 86 | 34.4 | 48 |

1.5 Genetic analysis

Segregation-analysis of ARM1 seeds on kanamycin-containing medium allowed to deduce the presence of only one T-DNA tagged locus.

1.6 Southern analysis of line ARM1.

DNA was extracted from the ARM1 line, using 0.2 to 2 g of plant material as described by Dellaporta et al. (1983) with some modification. The DNA pellets were dissolved in 400 μl TRIS EDTA to which 20 μg RNase was added. After an incubation period of 20 minutes at 37° C., 400 μl CTAB buffer (0.2 M Tris.Cl pH7.5, 2 M NaCl, 0.05 M EDTA. 2%

(w/v) CTAB) was added and the mixtures were further incubated for 15 minutes at 65° C. The samples were extracted with 800 µl chloroform/isoamylalcohol (24:1) and precipitated.

To determine the number of T-DNA inserted in line ARM1, purified total plant DNA was restricted with HindIII and EcoRI, either alone or combined in a double digest. Separation of the digested samples on a 1% agarose gel in TAE buffer was followed by an overnight blotting to a Hybond-N membrane (Amersham. U.K). The DNA on the membrane was fixed by U.V. cross linking (GS Gene Linker BioRad Laboratories, Hercules, Calif.). The 1.7 kb NruI fragment of pGUS1 (Peleman et al., 1989) comprising the coding region of the uidA gene, was used as a probe. Radioactive labelling was performed using the Ready-To-Go® DNA labelling kit (Pharmacia) according to the manufacturer's instructions. The nylon membrane was incubated in a hybridization buffer (3× standard sodium citrate buffer, 0.1% sodium dodecyl sulphate, 0.25% skim milk powder and 20 µg/ml herring sperm DNA) for 3 hours at 65 °C. Hybridization was performed overnight in fresh hybridization buffer to which the $\alpha^{32}$P-dCTP labelled probe was added.

Further Southern analysis, using several restriction enzymes, allowed to determine that 2 intact T-DNA copies were present in reverse direction with the two right borders linked together and that a third incomplete T-DNA copy, integrated at a different locus was present. The T-DNA copy at the second locus does not comprise an nptll gene and segregates independently from the first locus which is responsible for the characteristic gus expression pattern described above.

Example II

Isolation and analysis of the promoter tagged in ARM1.

The promoter tagged in line ARM1 is switched on early in the development of the fixed feeding sites: consequently it constitutes an excellent promoter to express a protein at an early stage of infection.

Due to the fact that the two T-DNA-copies in line ARM1 are present in inverted repeat linked together at their right border, the observed gus expression can be the result of transcription from within the plant sequences adjacent to either of the two promoter-less uidA gene copies. Hence both plant DNA sequences need to be evaluated for their transcription promoting activity.

2.1. Isolation of the plant sequences adjacent to the T-DNA insertions in ARM1:

Plant sequences adjacent to the T-DNA insertions in ARM1 were isolated by inverse PCR (iPCR). Plant DNA isolated from line ARM1 as described was digested with Sspl and EcoRI respectively, and ligated in conditions favouring selfligation (Sambrook et al., 1989). The ligation mixtures were used as templates for PCR, using a primer complementary to a sequence located closely to the left border of the T-DNA [primer 1 (SEQ ID No. 1) and either primer 2 ( SEQ ID No. 2) for the SspI digested templates, or primer 3 (SEQ ID No 3) for the EcoRI digested templates]. The following conditions were used for the PCR reaction: 50 ng template DNA. 200 ng of each primer, 25 mM MgCl$_2$, 10 mM dNTP's. 2.5 µl 10× Taq-buffer, 0.5 µl Taq polymerase (5 U/pl) in a total volume of 25 µl overlayed with 25 µl mineral oil. A total of 35 cycles were used. For both primer sets 1–2 and 1–3, the same temperature program was followed with an exception for the annealing temperature being 64° C. and 60° C. respectively. Cycle order was a first cycle comprising 4 min at 95° C., 2 min at 64° C./60° C., 10 min 72° C., followed by 34 cycles comprising 1 min at 95° C., 2 min at 64° C./60° C., 3 min at 72° C., finally followed by 10 min at 72° C. A fragment of 633 bp (ARM1-a) was isolated from the PCR reaction using Ssp/digested. self-ligated DNA as template, while a fragment of about 2500 bp (ARM1-b) was isolated from the PCR reaction using EcoRI digested, self-ligated DNA as template.

Both iPCR generated fragments were cloned in the pGEM®-T vector (Promega) following the manufacturers instructions, resulting in clones pARM1a and pARM1b. ARM1a was sequenced and the nucleotide sequence is represented in SEQ ID No. 4.

2.2. Isolation of the genomic clones comprising the T-DNA insertion point in ARM1a and sequence analysis.

The ARM1a fragment recovered by iPCR as described in 2.1 was used as a radioactively labelled probe (described above) to isolate the corresponding genomic clones from an *A. thaliana* library constructed in the vector Charon 35. designated RUG-AT2 (as described by Gheysen et al. 1991). Four positive phage clones (Ch/ARM1A, Ch/ARM1B, Ch/ARM1C and Ch/ARM1D) were isolated and analysed by restriction mapping and Southern analysis leading to an arrangement of the clones to yield the restriction map of the chromosomal locus T-DNA tagged in the line ARM1. An XbaI fragment of about 3.5 kb. hybridizing to both T-DNA/plant border fragments isolated by iPCR was cloned in pBlueScript, yielding Ch/ARM1D3500. This clone was used to isolate the larger fragments comprising the DNA sequences corresponding to ARM1a nucleotide sequences in the promoter analysis described below. Sequence analysis of the region surrounding the T-DNA insertion locus yielded the DNA sequence represented in SEQ ID No. 5.

Comparison of the nucleotide sequence of iPCR generated ARM1a. ARM1b and the genomic sequence revealed a rearrangement of plant DNA upon insertion. Such rearrangements are not uncommon with T-DNA integration (Gheysen et al., 1991). The T-DNA insertion site was pinpointed to nucleotide 1444 of SEQ ID No. 5. This insertion occurs within an ORF of at least 50 amino acids, whose ATG is located at nucleotide positions 1418–1420 of SEQ ID No. 5. No significant homology was detected when the amino acid sequence of this ORF was used as a query sequence in database searches.

2.3. Deletion analysis and description of 0.5 kb promoter and 3.7 kb promoter.

To locate the nematode-induced promoter genetically, different constructs comprising genomic sequences upstream of the T-DNA insertion were cloned in front of a promoterless uidA gene with a plant intron (Van Canneyt et al., 1990), fused to a CaMV35S 3' end formation and polyadenylation signal. All DNA constructs for promoter analysis were performed using pTHW136.

pTHW136 was constructed in the following way. An about 2.4 kb BamHI DNA fragment comprising the nos promoter-nptll-3' ocs cassette was inserted in pGSV5. yielding pGSV6. A HindIII fragment from p35SGUSINT comprising the CaMV35S promoter operably linked to a uidA gene containing a plant intron (Van Canneyt et al., 1990) was introduced into the HindIII site of pGSV6.The CaMV35S promoter can easily be replaced in this T-DNA vector by replacing the about 0.4 kb XbaI fragment, pGSV5 was derived from plasmid pGSC1700 (Cornelissen and Vandewiele, 1989) but differs from the latter in that it does not contain a β-lactamase gene and that its T-DNA is characterized by the sequence of SEQ ID No 9.

A first plasmid was constructed by cloning in the correct orientation, the PvuII-SspI fragment of pARM1a comprising the nucleotide sequence of SEQ ID No. 4 from nucleotide position 45 to 573 in pTHW136. which had been digested by XbaI and treated with Klenow polymerase.

The introduced fragment comprises a nucleotide sequence corresponding to the nucleotide sequence of SEQ ID No. 5 from nucleotide position 1055 to 1444. This T-DNA was inserted in *A. thaliana* via Agrobacterium-mediated transformation as described above. Transgenic lines were analysed for (nematode-induced) gus-expression as described above. GUS-staining upon inoculation with *M. incognita* was detected in the nematode feeding cells as for the original line ARM1, both in pattern and timing, but the intensity of the staining was weaker and overnight incubation was required to obtain a clearly visible response. No GUS-staining was detected in plant tissues outside of the nematode feeding cells.

Since the about 0.5 kb region apparently directed a gus expression that corresponded in timing and pattern of the nematode induction to that of the original ARM1 line, yet was weaker, a larger upstream fragment of the genomic sequence was included. To this end novel primers were designed such as MAKAR 17 (SEQ ID No. 7) and MAKAR4 (SEQ ID No. 6) and used to amplify by PCR (with Pfu polymerase; Stratagene) specifically the T-DNA/plant DNA border fragment without having to resort to iPCR. The nucleotide sequence of this PCR amplified fragment is represented in SEQ ID No. 8. This fragment was cloned in the EcoRV site of pBlueScript II KS (Stratagene), yielding plasmid pARM1a1300. Although two possible orientations of the insert in the vector are possible, a person skilled in the art will recognize which one will suit his needs for the further cloning. A SmaI fragment [comprising the nucleotide sequence of SEQ ID No. 8 from nucleotide at positions 1 to 1190: the SmaI site upstream of nucleotide 1 of SEQ ID No. 8 is located in the multicloning site (MCS) of pBlueScript II KS] comprising the genomic sequences corresponding to of SEQ ID No. 5 from nucleotide at positions 945 to 1444 was excised and cloned in the proper orientation in pTHW136. which had been digested by XbaI and treated with Klenow polymerase, in front of the promoterless uidA gene. This T-DNA was inserted in *A. thaliana* via Agrobacterium-mediated transformation as described above. Transgenic lines were analyzed for (nematode-induced) gus expression as described above. GUS-staining upon inoculation with *M. incognita* was detected in the nematode feeding cells as for the original line ARM1, both in pattern and timing, but the intensity of the staining was weaker and overnight incubation was required to obtain a clearly visible response. No GUS-staining was detected in plant tissues outside of the nematode feeding cells.

A chimeric gene comprising about 3.1 kb of upstream sequences of the ARM1a T-DNA/plant DNA border junction in front of a promoterless uidA gene was cloned by exchanging the about 360 bp PstI/StyI fragment of pARM1a1300 (PstI is located in the MCS of pARM1a1300) for the about 3 kb PstI/StyI from Ch/ARM1 D3500. resulting in pARM1a3500. A SmaI fragment of about 3.7 kb comprising the promoter can be excised from pARM1a3500 and inserted in the proper orientation in pTHW136, which had been digested by XbaI and treated with Klenow polymerase, in front of the promoterless uidA gene. This T-DNA was inserted in *A. thaliana* via Agrobacterium-mediated transformation as described above. Transgenic lines were analyzed for (nematode-induced) gus expression as described above. GUS-staining upon inoculation with *M. incognita* was detected in the nematode feeding cells as for the original line ARM1, both in pattern and timing, and level of expression approximated that of the original ARM1 line. A 5 hour incubation of the GUS-staining reaction was sufficient to obtain a clearly visible response.

Example 3

Construction of nematode-inducible chimeric genes.

For the construction of chimeric nematode-inducible genes, which when integrated in the genome of a plant, result in improved nematode resistance, three DNA fragments (with blunt ends) comprising a nematode-inducible promoter are used:

NIP1: the about 460 bp SspI/PvuII fragment of pArm1a

NIP2: the about 1.3 kb SmaI fragment of pArm1a1300

NIP3: the about 3.7 kb SmaI fragment of pARM1a3500

Using the above-identified promoter fragments, chimeric genes are constructed with different first foreign DNA regions to be expressed at the sites of nematode infection. Construction of a chimeric gene carrying a barnase coding region under control of the nematode-inducible promoter.

A nematode-inducible chimeric gene (NIP2-barnase-3' nos) is constructed comprising the following operably linked DNA fragments:

NIP2: the 5' regulatory region as described above comprising a nematode-inducible promoter.

barnase a DNA fragment coding for barnase of *Bacillus amyloliquefaciens* (Hartley, 1988), 3' nos NIP2-barnase-3' nos between T-DNA border repeats was constructed by replacing the pTA29 promoter upstream of the barnase coding region in pTC099. by the nematode-inducible promoter cassette NIP2. To this end the about 1.3 kb SmaI fragment from pAAA (NIP2) was fused to the blunted NcoI site overlapping with the ATG-codon which had been engineered at the 5' end of the coding sequence for the mature barnase in pTCO99. resulting in the plasmid vector pNIP2B1 carrying the NIP2-barnase-3' nos chimeric gene between the T-DNA border repeats. The T-DNA vector part of pTC099 is derived from that of pGSV5 by insertion of an EcoRI linker (GGAATTCC) into the SmaI site of the polylinker, and a Bg/ll linker (CAGATCTG) into the NcoI site of the polylinker followed by introduction of the chimeric pTA29-barnase-3' nos gene of pTCO113 [WO96/26283] into the EcoRI site of the polylinker.

Subsequently the Bg/ll fragment of pTCO113 [WO96/26283] comprising the barstar coding region under control of nopaline synthase promoter (pnos-barstar-3' g7) is inserted into the polylinker of pNIP2B1 between the T-DNA border repeats, resulting in pNIP2B2. Introduction of the chimeric selectable marker gene pSSUAra-bar-3' g7 in the polylinker sequence of pNIP2B2 between the T-DNA border repeats results in pNIP2B3.

Another nematode-inducible chimeric gene (NIP3-barnase-3' nos) is constructed comprising the following operably linked DNA fragments:

NIP3: the 5' regulatory region as described above comprising a nematode-inducible promoter.

barnase: a DNA fragment coding for barnase of *Bacillus amyloliquefaciens* (Hartley, 1988).

3' nos

NIP3-barnase-3' nos between T-DNA border repeats was constructed by replacing the pTA29 promoter upstream of the barnase coding region in pTC099, by the nematode-inducible promoter cassette NIP3. To this end the about 3.7 kb SmaI fragment from pBBB (NIP3) was fused to the blunted NcoI site overlapping with the ATG-codon which had been engineered at the 5' end of the coding sequence for the mature barnase in pTCO99. resulting in the plasmid vector pNIP3B1 carrying the NIP3-barnase-3' nos chimeric gene between the T-DNA border repeats.

Subsequently the Bg/ll fragment of pTCO113 [WO96/26283] comprising the barstar coding region under control of nopaline synthase promoter (pnos-barstar-3' g7) is inserted into the polylinker of pNIP3B1 between the T-DNA border repeats, resulting in pNIP3B2. Introduction of the chimeric selectable marker gene pSSUAra-bar-3' g7 in the polylinker sequence of pNIP3B2 between the T-DNA border repeats results in pNIP3B3.

Construction of a chimeric gene carrying a Proteinase inhibitor coding region (oryzacystatin-1) under control of the nematode-inducible promoter.

To operably link the above described nematode-inducible promoters to OC-1, a DNA fragment coding for oryzacystatin-1 of *Oryza sativa*, a SmaI/EcoRI DNA fragment of about 300 bp comprising the OC-1 coding region without intron was amplified by PCR from genomic DNA of *Oryza sativa L. japonica* as described in detail in EP 0 502 730 and the about 300 bp SmaI/EcoRI fragment is cloned in pBluescriptII Ks (Promega), resulting in pOCI. The DNA fragments comprising the nematode-inducible promoters as described above (NIP1, NIP2 and NIP3) are inserted as an about 300 bp SspI/PvuII fragment, an about 1300 bp SmaI fragment and an about 3500 bp SmaI fragment respectively, yielding pNIP1OCl. pNIP2OCl and pNIP3OCl respectively. The cassette comprising the operably linked nematode-inducible promoter and OC-1 coding region are excised using appropriate restriction enzyme digest. The respective nematode-inducible genes and the marker gene (pSSU-bar-3' ocs De Almeida et al., 1989) are introduced in the polylinker between the border sequences of the T-DNA vector pGSV5, yielding pTNIP1OCl, pTNIP2OCl and pTNIP3OCl respectively.

The T-ONA vectors comprising the nematode-inducible chimeric genes (pTNIP1OCl, pTNIP2OCl and pTNIP3OCl. pNIP2B3 and pNIP3B3) are introduced in *Agrobacterium tumefaciens* C58C1Rif$^R$ (Holsters et al., 1980) carrying:

a helper Ti-plasmid pMP90 (Koncz and Schell, 1986) or a derivative thereof (such as pGV4000), which is obtained by insertion of a bacterial chloramphenicol resistance gene linked to a 2.5 kb fragment having homology with the T-DNA vector pGSV5, into pMP90.

Example 4

Production of nematode-resistant potato plants.

The respective Agrobacterium strains of Example 3 are used to transform potato plants (*Solanum tuberosum* cvs Bintje and Désiré) by means of tuber disc infection as described by De Block et al., (1987).

Example 5

Production of nematode-resistant oilseed rape plants.

Hypocotyl explants of *Brassica napus* are obtained, cultured and transformed essentially as described by De Block et al. (1989), except for the following modifications:

hypocotyl explants are precultured for 3 days in A2 medium [MS. 0.5 g/l Mes (pH5.7), 1.2% glucose, 0.5% agarose, 1 mg/l 2.4-D. 0.25 mg/l naphthalene acetic acid (NM) and 1 mg/l 6-benzylaminopurine (BAP)].

infection medium A3 is MS, 0.5 g/l Mes (pH5.7), 1.2% glucose, 0.1 mg/l NAA, 0.75 mg/l BAP and 0.01 mg/l gibberellinic acid (GA3).

selection medium A5 is MS, 0.5 g/l Mes (pH5.7), 1.2% glucose, 40 mg/l adenine, SC$_4$, 0.5 g/l polyvinylpyrrolidone (PVP), 0.5% agarose. 0.1 mg/l NAA. 0.75 mg/l BAP, 0.01 mg/l GA3. 250 mg/l carbenicillin, 250 mg/l triacillin, 0.5 mg/l AgNO$_3$.

regeneration medium A6 is MS, 0.5 g/l Mes (pH5.7), 2% sucrose, 40 mg/l adenine, SO$_4$, 0.5 g/l PVP, 0.5% agarose, 0.0025mg/l BAP and 250 mg/l triacillin.

healthy shoots are transferred to rooting medium which was A8: 100–130 ml half concentrated MS, 1% sucrose (pH5.0), 1 mg/l isobutyric acid (IBA), 100 mg/l triacillin added to 300 ml perlite (final pH6.2) in 1 liter vessels.

MS stands for Murashige and Skoog medium (Murashige and Skoog, 1962)

Hypocotyl explants are infected with *Agrobacterium tumefaciens* strain C58C1Rif$^R$ carrying:

a helper Ti-plasmid pMP90 (Koncz and Schell, 1986)or a derivative thereof (such as pGV4000).

the T-DNA vectors comprising the nematode-inducible chimeric genes (pTNIP1OCl, pTNIP2OCl and pTNIP3OCl, pNIP2B3 and pNIP3B3)

Example 6

Analysis of transformed plants.

The transgenic potato plants of Example 4 and the transgenic oilseed rape plants of Example 5, are infected with *Globodera pallida* (as described by Urwin et al., 1995) or *Heterodera schachtii* (as described above.)

Two weeks after infection, the root system can be scored visually for the number of successful infections and compared to untransformed plants. Plant lines are considered resistant when they show a significantly decreased susceptibility to plant pathogenic nematodes (i.e. a significant decrease in the number of females found on roots of transgenic plants carrying the chimeric genes of the invention, versus the number of (egg-laying) females found on the roots of control plants) and/or when the number of nematode feeding sites is significantly reduced when compared with control plants and/or when egg production is significantly reduced. Susceptible/resistance classification according to the number of maturing females is standard practice both for cyst- and root-knot nematodes (e.g. LaMondia, 1991; Omwega et al., 1990)

Analysis of selected plant lines shows a lower level of female nematodes and the presence of fewer nematode-feeding sites in the transgenic plants due to expression of the chimeric genes of Example 3.

The potato plants of Example 4 are more resistant to infection with *G. pallida, G. rostochiensis,* and Meloidogyne species.

The oilseed rape plants of Example 5 are more resistant to infection with *Heterodera schachtii*.

Needless to say, the use of the nematode-inducible promoters and chimeric genes of this invention is not limited to the transformation of the specific plants of the examples. It is expected that such promoter and chimeric gene constructs are useful in transforming any crop wherein the promoter can control gene expression, preferably where such expression occurs abundantly in the nematode feeding site cells.

Also, the use of the nematode-inducible promoters of the invention is not limited to the control of particular transcribed DNA regions of the invention, but can be used to control expression of any foreign DNA gene or DNA fragment in a plant. Furthermore, the present invention is not limited to the specific nematode-inducible promoters described in the above Examples. Rather, the present invention encompasses promoters, equivalent to the ones in the Examples, which can be used to control the expression of a structural gene, at least substantially selective in cells of nematode fixed feeding sites. Indeed, the DNA sequences of the nematode-inducible promoters of the Examples can be modified by replacing some of their nucleotides by other nucleotides and/or deleting or inserting some nucleotides provided that such modifications do not alter substantially the timing, level and tissue-specificity of expression controlled by the promoter, as measured by GUS-assays in transgenic plants transformed with a chimeric uidA gene under control of the modified promoter (see Example 2). Up to 20% of the nucleotides of a promoter may be changed without affecting the characteristics of the promoter.

All publications (including patent publications and database entries) cited in this application are hereby incorporated by reference to the extent possible by national or regional laws.

Plasmids pARM1a. Pch/ARM1D3500, pARM1a1300 and pARM1a3500 have been deposited at the Belgian Coordinated Collections of Microorganisms (BCCM)

Laboratorium voor Moleculaire Biologie-Plasmidecollectie (LMBP)

Universiteit Gent

K. L. Ledeganckstraat 35

B-9000 Gent, Belgium on Dec. 10, 1996 and have been attributed the following deposition numbers:

DH5α(pARM1a): BCCM/LMBP3638
XL1-Blue(pchARMD3500): BCCM/LMBP3635
XL1-Blue(pARM1a1300): BCCM/LMBP3636
XL1-Blue(pARM1a3500): BCCM/LMBP3637

REFERENCES

Barthels et al. (1994) *Med. Fac. Landbouww. Univ. Gent* 59/2b: 757–762

Beeckman and Engler (1994) *Plant. Mol. Biol. Rep.* 12(1): 37–42

Benfey and Chua (1990) *Science* 250: 959–966

Bouchez et al. (1993) C. R. Acad. Sci Parise, *Sciences de la vie* 316: 1188–93

Chitwood and Lusby (1991) *Lipids* 26: 619–627

Clarke et al. (1992) *Plant Mol. Biol. Rep.* 10(2): 178–189

Cornelissen and Vandewiele (1989) *Nucl. Acids Res.* 17: 833

De Almeida et al. (1989) *Mol. Gen. Genet.* 218: 78–86

Deblaere et al. (1985) *Nucl. Acids Res.* 13: 4777–4788

De Block et al. (1987) *EMBO J.* 6: 2513–2518

De Block et al. (1989) *Plant Physiol.* 91: 694–701

De Greve er al. (1982) *J. Mol. Appl. Genet.* 1: 499–511

Dellaporta et al. (1983) *Plant. Mol. Biol. Rep.* 1:19–21

Depicker et al. (1982) *J. Mol. Appl. Genet.* 1: 561–573

Fromm et al. (1990) *Bio/Technology* 8: 833–839

Gheysen et al. (1991) *Genes and Development* 5: 287–297

Goddijn et al. (1993) *The Plant Journal* 4(5): 863–873

Gordon-Kamm et al. (1990) *The Plant Cell* 2: 603–618

Greenland et al. (1983) *Proc. Natl. Acad. Sci. USA* 80: 6853

Gurr et al (1991) *Mol. Gen. Genet.* 226: 361–366

Hartley (1988) *J. Mol. Biol.* 202: 913–915

Holsters et al. (1980) *Plasmid* 3: 212–230

Jefferson (1987) *Plant Mol. Biol. Rep.* 5(4): 387–405

Jones (1981) in *Plant Parasitic Nematodes* B. M. Zuckerman and R. A. Rohde eds (New York: Academic Press), vol 3: 255–278

Karimi et al. (1994) *Med. Fac. Landbouww. Univ. Gent* 59/2b: 751–756

Kertbundit et al (1991) *Proc. Natl. Acad. Sci. USA* 88: 5212–5216

Klap and Sijmons (1994) Abstract of the 22nd International Nematology Symposium, 7–12 Aug 1994. Gent Koncz and Scheil (1986) *Mol. Gen. Genet.* 204: 383–396

LaMondia (1991) *Plant disease* 75: 453–454

Mandal et al. (1995) *Plant Molecular Biology Reporter* 13 (3): 243–254

Marton and Browse (1991) *Plant Cell Rep.* 10: 235–239

Meyer et al. (1987) *Nature* 330: 677–678

Murashige and Skoog (1962) *Physiol. Plant.* 15: 473

Omwega et al. (1990) *Phytopathol.* 80: 745–748

Opperman et al. (1994) *Science* 263: 221–223

Peleman et al. (1989) *The Plant Cell* 1: 81–93

Sasser and Freckman (1987) in *Vistas on Nematology* Veech and Dickson eds. Society of Nematologists Sijmons et al. (1991) *The Plant Journal* 1(2): 245–254

Strittmatter et al. (1996) *Mol. Plant Micr. Interact.* 9, 68–73

Topping et al. (1991) *Development* 112, 1009–1019

Urwin et al. (1995) *The Plant Journal* 8, 121–131

Valvekens at al. (1988) *Proc. Natl. Acad. Sci USA* 85: 5536–5540

Valvekens et al. (1991) in *Plant Tissue Culture Manual: Fundamentals and Applications* ed. K. Lindsey. Kluwer Academic Publishers, Dordrecht Van Canneyt et al. (1990) *Mol. Gen. Genet.* 220: 245–250

Velten and Schell (1985) *Nucl. Acids Res.* 13: 6998–6998

Wilbur and Lipmann (1983) *Proc. Nat. Acad. Sci. U.S.A.* 80: 726

What is claimed is:

1. An isolated DNA fragment comprising the nucleotide sequence of SEQ ID No. 5 from nucleotide position 1055 to 1417.

2. An isolated DNA fragment comprising the nucleotide sequence of SEQ ID No. 4 from nucleotide position 46 to 408.

3. An isolated DNA fragment comprising the nucleotide sequence of SEQ ID No. 4 from nucleotide position 46 to 573.

4. An isolated DNA fragment comprising the DNA sequence of the 528 bp SspI-PvuII fragment of plasmid pARM1a (LMBP3638).

5. An isolated DNA fragment comprising the DNA sequence of the about 3 kb Pstl-Styl fragment of plasmid pch/ARM1 D3500 (LMBP3635).

6. An isolated DNA fragment comprising the DNA sequence of the about 3 kb Pstl-Styl fragment of plasmid pch/ARM1D3500 (LMBP3635) and the DNA sequence of SEQ ID No. 8 from nucleotide position 367 to 1190.

7. An isolated DNA fragment comprising the DNA sequence of the about 3 kb Pstl-Styl fragment of plasmid pARM1a3500 (LMBP3637) and the DNA sequence of SEQ ID No. 4 from nucleotide position 46 to 408.

8. An isolated DNA fragment comprising the DNA sequence of the about 2.5 kb Pstl-Sspl fragment of plasmid pARM1a3500 (LMBP3637) and the DNA sequence of SEQ ID No. 4 from nucleotide position 46 to 573.

9. An isolated DNA fragment comprising the about 1.3 kb Smal fragment of plasmid pARM1a1300 (LMBP3636).

10. An isolated DNA fragment comprising the DNA sequence of SEQ ID No. 8.

11. An isolated DNA fragment comprising the about 3.7 kb Smal fragment of plasmid pARM1a3500 (LMBP3637).

12. An isolated DNA fragment comprising a nucleotide sequence which is 95% similar to the nucleotide sequence of SEQ ID NO. 4 from nucleotide position 46 to 408, wherein said sequence identity is determined by alignment performed with the Wilbur and Lipmann algorithm using a window size of 20 nucleotides, a word length of 4 nucleotides, and a gap penalty of 4, wherein said DNA fragment controls the expression of foreign DNA in a fixed feeding site of a sedentary nematode-infected plant.

13. A chimeric gene comprising the follow operably linked DNA fragments:
   a. a plant-expressible promoter region comprising the DNA fragments of claim 1;
   b. a foreign DNA region;
   c. a 3' end formation and polyadenylation signal functional in plant cells.

14. The chimeric gene of claim 13, wherein said foreign DNA region encodes β-glucuronidase.

15. The chimeric gene of claim 13, wherein said foreign DNA region encodes a proteinase inhibitor.

16. The chimeric gene of claim 13, wherein said foreign DNA region encodes barnase.

17. A plant cell comprising the chimeric gene of claim 13.

18. A plant cell comprising the chimeric gene of claim 16, wherein said plant further comprises a second chimeric gene comprising a barstar coding region under control of a plant expressible promoter.

19. A plant comprising the chimeric gene of claim 13 integrated in its genome.

20. The plant of claim 19 which is a potato plant.

21. The plant of claim 19 which is an oilseed rape plant.

22. A method for preventing nematode-attack of a plant, comprising cultivating a plant comprising an introduced foreign DNA which comprises the DNA of claim 13 in a field.

23. A method for combatting plant pathogens, which comprises expressing a foreign DNA in a plant under the control of a promoter region comprising the DNA fragment of any one of claims 1 to 12.

24. The method of claim 23 wherein said pathogen is a pathogen of plant roots.

25. An isolated DNA fragment of claim comprising a nucleotide sequence which has a 95% nucleotide sequence identity with the nucleotide sequence of SEQ ID No. 4 from nucleotide position 46 to 408 and which is a nematode-induced promoter sequence.

26. A plant promoter which is induced by nematodes, wherein the isolated DNA fragment of claim 1 comprises said promoter.

\* \* \* \* \*